(12) United States Patent
Chen et al.

(10) Patent No.: US 7,683,208 B2
(45) Date of Patent: Mar. 23, 2010

(54) BRIDGE COMPOUND WITH N,N-DIALKYLAMINO GROUP AND APPLICATION THEREOF

(75) Inventors: Wen-Jang Chen, Taoyuan Hsien (TW); Hong-Chang Huang, Taoyuan Hsien (TW); Chien-Yu Chen, Taoyuan Hsien (TW); Ya-Cing Yu, Taoyuan Hsien (TW); Chen-Lung Kao, Taoyuan Hsien (TW); Carolin Michaela Mueller, Manchester (GB)

(73) Assignee: Everlight USA, Inc., Pineville, NC (US)

( * ) Notice: Subject to any disclaimer, the term of this patent is extended or adjusted under 35 U.S.C. 154(b) by 60 days.

(21) Appl. No.: 12/071,314

(22) Filed: Feb. 20, 2008

(65) Prior Publication Data

US 2009/0054645 A1 Feb. 26, 2009

(30) Foreign Application Priority Data

Aug. 23, 2007 (CN) .................. 2007 1 0147535

(51) Int. Cl.
*C07C 317/34* (2006.01)
(52) U.S. Cl. ........................................ 562/67; 564/341
(58) Field of Classification Search ........................ None
See application file for complete search history.

(56) References Cited

U.S. PATENT DOCUMENTS 5,079,248 A * 1/1992 Cross et al. .............. 514/237.5

7,619,074 B2 * 11/2009 Chen et al. .................. 534/629

OTHER PUBLICATIONS

Cross et al., Chemical Abstracts, 112:138682, 1990.*
v. Braun et al., Chemical Abstracts, 18:6051, 1924.*
Cross et al., Journal of Medicinal Chemistry, 33(4), 1151-1155, 1990.*

* cited by examiner

*Primary Examiner*—Fiona T Powers
(74) *Attorney, Agent, or Firm*—Bacon & Thomas, PLLC

(57) ABSTRACT

The present invention relates to a bridge compound with an N,N-dialkylamino group, represented by the following formula (I),

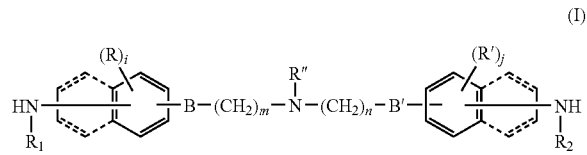

wherein, R, R', R", $R_1$, $R_2$, B, B', i, j, m, and n are defined the same as the specification. The novel bridge compound of the present invention is suitable for being used as a bridge group between dyestuffs, ultraviolet absorbers, or one dyestuff and one ultraviolet absorber. In addition, the present invention further provides a dyestuff compound provided from the aforementioned bridge compound.

14 Claims, No Drawings ly used for high-temperature exhaustion dyeing. However, CI Reactive Red 141 exhibits poor levelness in low-concentration dyeing.

US 7,683,208 B2

BRIDGE COMPOUND WITH N,N-DIALKYLAMINO GROUP AND APPLICATION THEREOF

BACKGROUND OF THE INVENTION

1. Field of the Invention

The present invention relates to a novel bridge compound with N,N-dialkylamino group and a dyestuff compound provided from the same.

2. Description of Related Art

CI Reactive Red 141 is represented by the following formula (a).

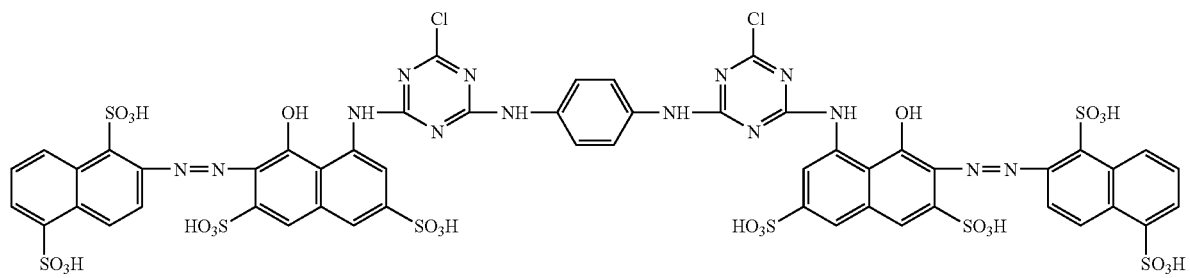

CI Reactive Red 141 is a reactive red dyestuff compound having two monochloro triazinyl reactive groups, and generally used for high-temperature exhaustion dyeing. However, CI Reactive Red 141 exhibits poor levelness in low-concentration dyeing.

The inventors discovered that the poor properties of CI Reactive Red 141 are caused by the bridge group of 1,4-benzenediamine, and thereby the inventors were devoted to the study of novel bridge groups.

SUMMARY OF THE INVENTION

The present invention provides a novel bridge compound, which is suitable for being used as a bridge group between, for example, dyestuffs, ultraviolet absorbers, or one dyestuff and one ultraviolet absorber.

The novel bridge compound with N,N-dialkylamino group of the present invention is represented by the following formula (I):

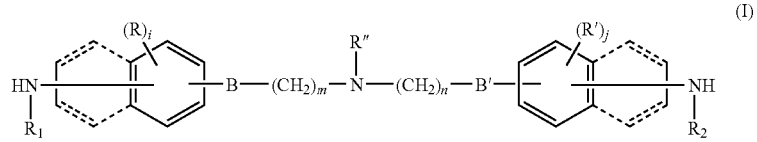

wherein,
R and R' each independently are selected from the group consisting of hydrogen, halogen, hydroxyl, carboxyl, sulfo, nitro, cyano, $C_{1-4}$ alkyl, $C_{1-4}$ alkoxy, ureido and amido;
$R_1$ and $R_2$ each independently are hydrogen, or $C_{1-4}$ alkyl;
R" is hydrogen, $C_{1-4}$ alkylcarbonyl, phenyl, $C_{1-4}$ alkyl, or $C_{1-4}$ alkyl substituted by halogen, hydroxyl, carboxyl or sulfo;

B and B' each independently are selected from the group consisting of a bond, —$SO_2$— and —CONH—$(CH_2)_n$—$SO_2$—;
i and j are integers independent of one another between 0 to 3; and
m and n are integers independent of one another between 2 to 4.

More preferably, the compound of the formula (I) of the present invention is the compound of the following formula (Ia),

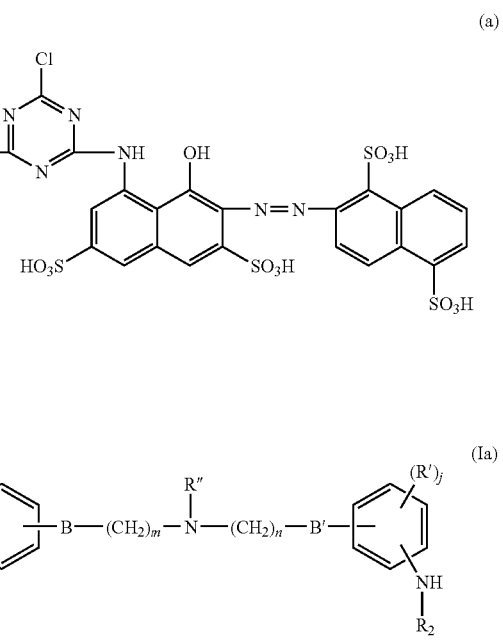

wherein, R, R', R", $R_1$, $R_2$, B, B', i, j, m and n are defined the same as above.

In the compound of the formula (I) according to the present invention, preferably, R and R' each independently are selected from the group consisting of hygrogen, sulfo, methyl and methoxy.

In the compound of the formula (I) according to the present invention, preferably, R" is selected from the group consisting of hydrogen, methyl, ethyl, —$C_2H_4OH$, —$C_2H_4SO_3H$, —$COCH_3$ and phenyl.

In the compound of the formula (I) according to the present invention, preferably, i and j each independently are 1 or 2.

In the compound of the formula (I) according to the present invention, preferably, m and n each independently are 2 or 3.

The compound of the formula (I) of the present invention can be prepared by the following synthetic routines:

(1) the addition reaction is performed between the compound of the formula (II) and the compound of the formula (III),

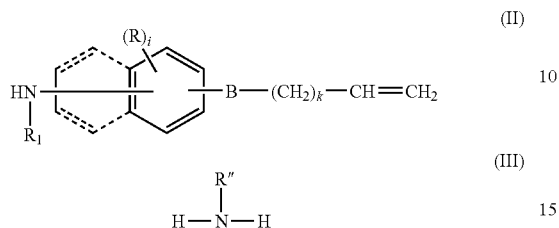

and the symmetric compound of the formula (IV) is obtained in a suitable reaction condition; or

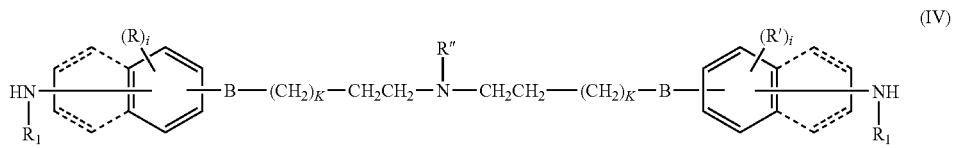

(2) the addition reaction is performed between the compound of the formula (II) and the compound of the formula (III), and the compound of the formula (V)

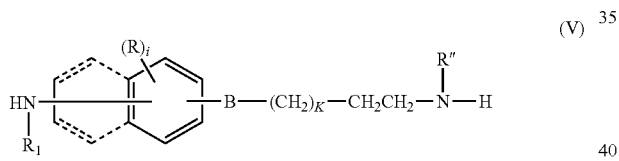

is obtained in a suitable reaction condition, and subsequently, the compound of the formula (V) reacts with the compound of the formula (VI) to afford the asymmetric compound of the formula (VII); or

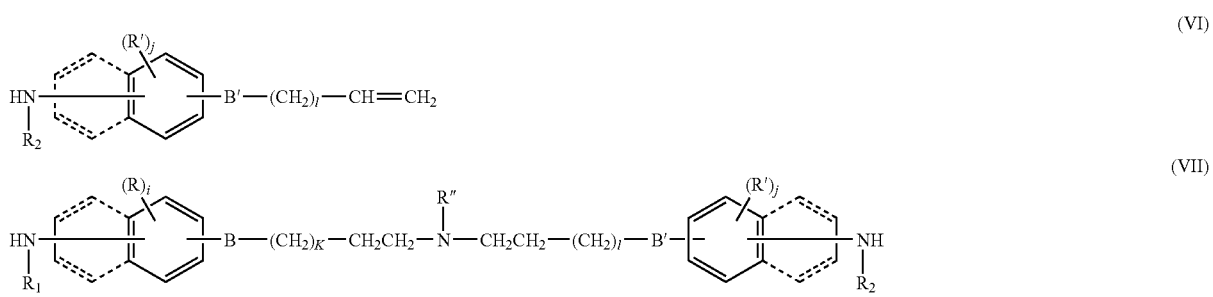

(3) the addition reaction is performed between the mixture consisting of the compounds (II) and (VI) in a suitable ratio and the compound of the formula (III) in a suitable reaction condition to afford the asymmetric compound of the formula (VII),

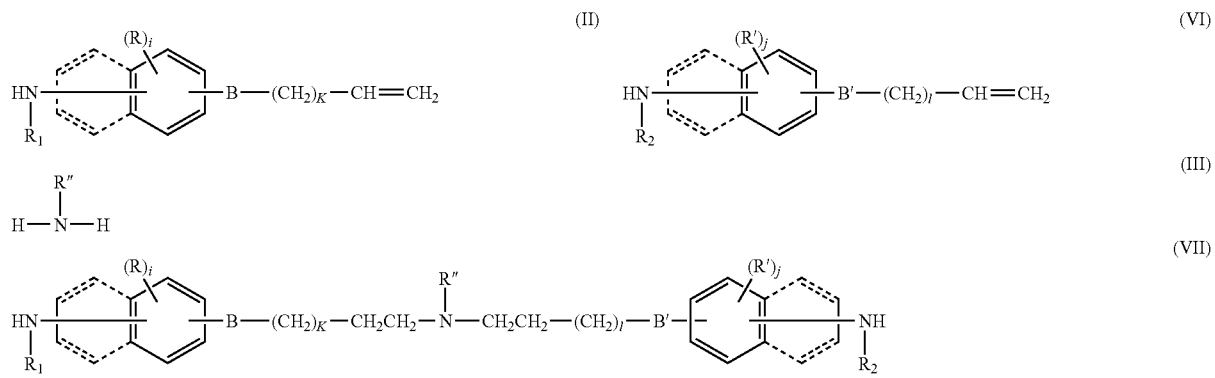
as well as the symmetric compounds (IV) and (VIII), owing to different bonding forms.
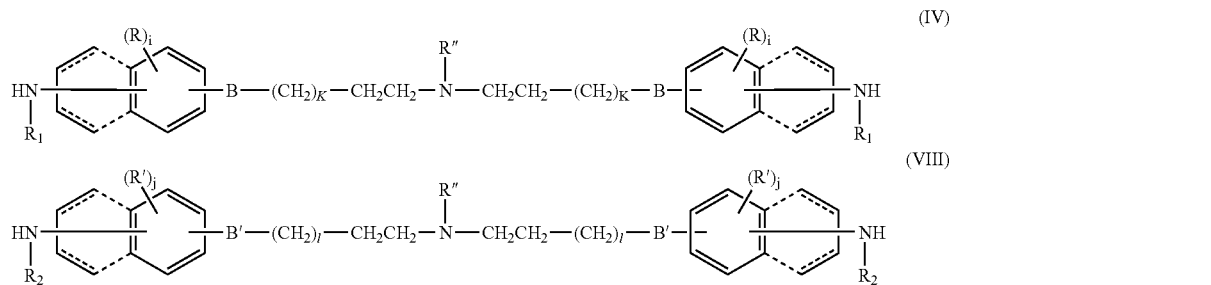
Herein, R, R', R", $R_1$, $R_2$, B, B', i, and j are defined the same as above, and k and l are integers independent of one another between 0 to 2.
Specific examples of the compound (I) according to the present invention are shown as follows, but not limited thereto:
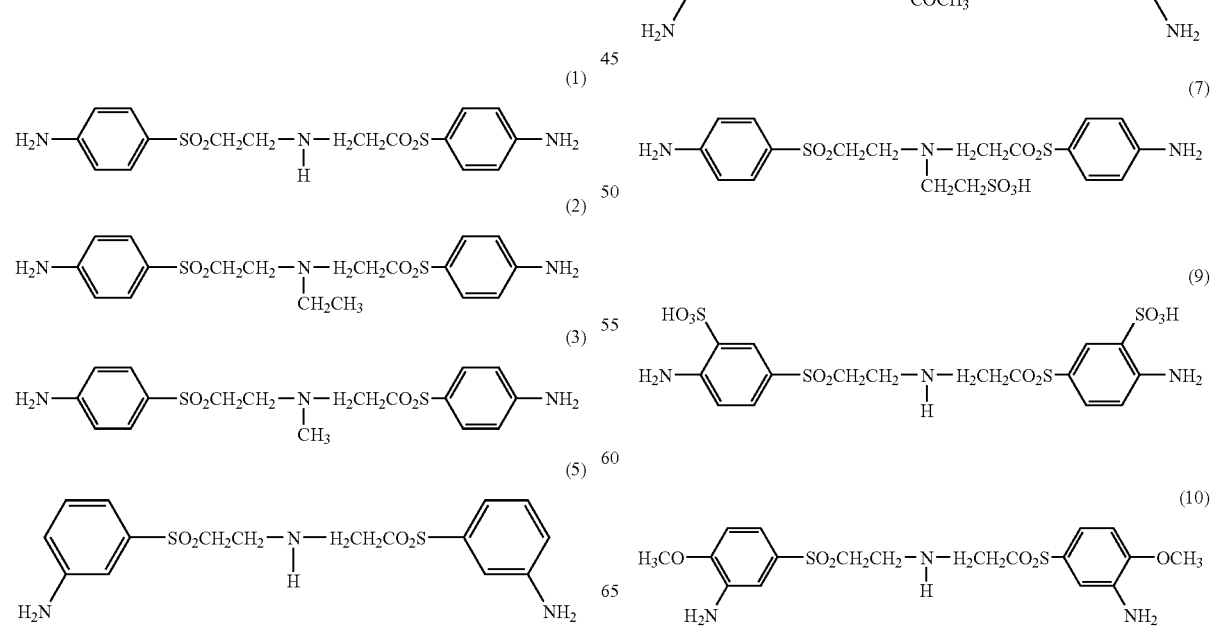

-continued
(14)
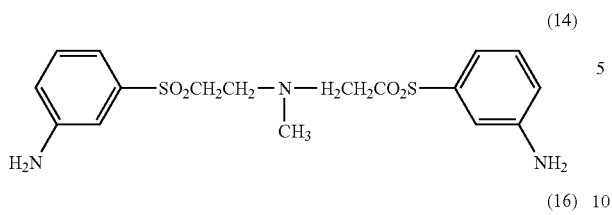
(16)
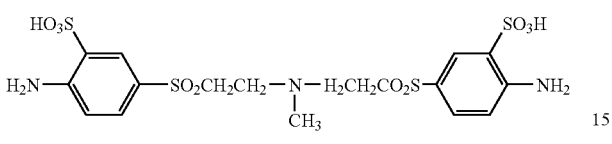
(17)
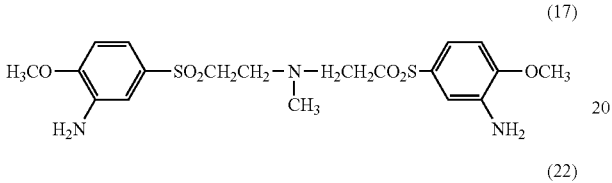
(22)
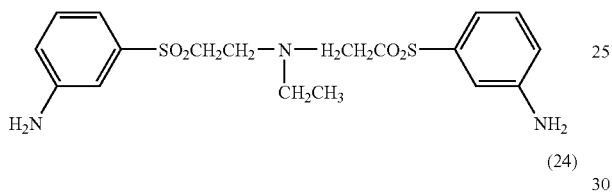
(24)
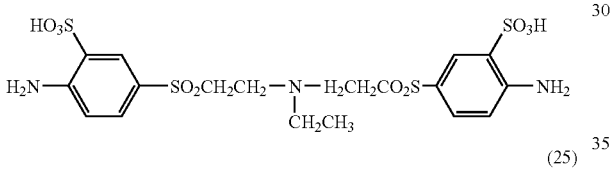
(25)
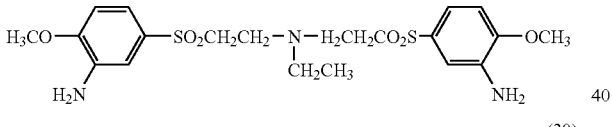
(30)
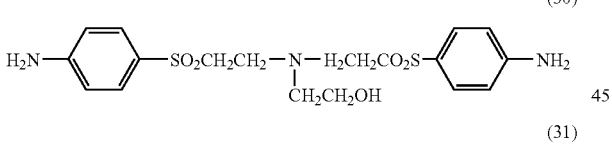
(31)
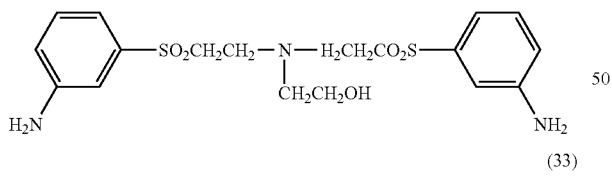
(33)
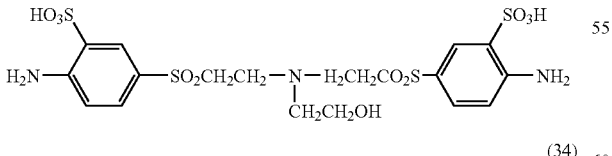
(34)
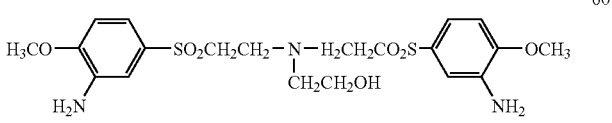
-continued
(39)
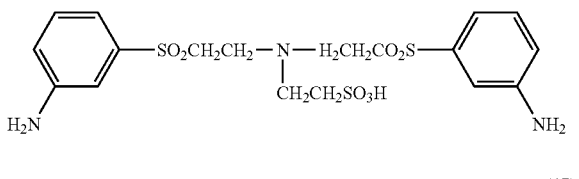
(47)
(48)
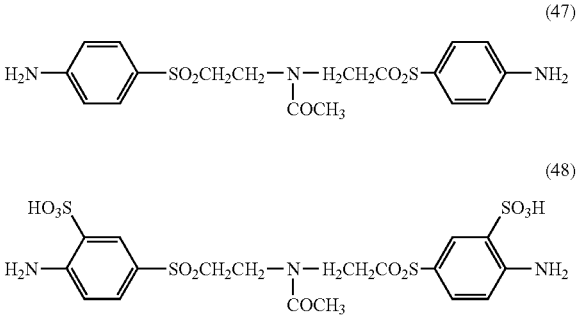
(52)
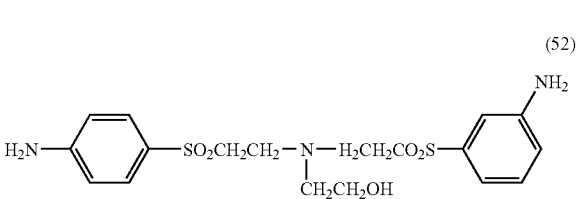
(53)
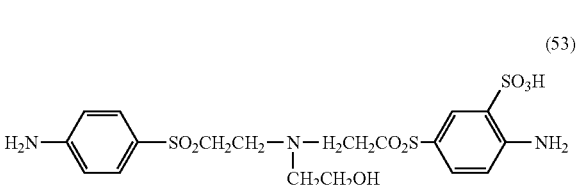
(54)
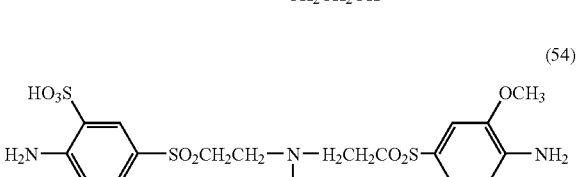
(55)
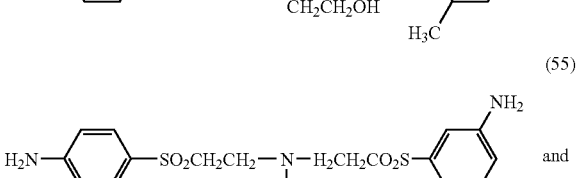
and
(56)
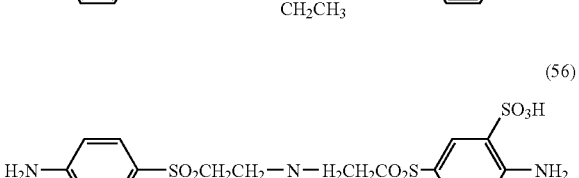
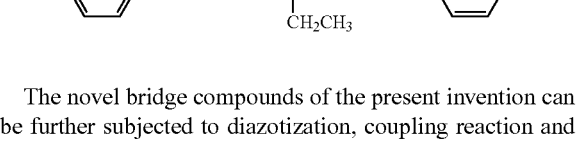
The novel bridge compounds of the present invention can be further subjected to diazotization, coupling reaction and condensation to provide dyestuff compounds.
Specific examples of the dyestuff compounds according to the present invention are shown as follows, but not limited thereto:

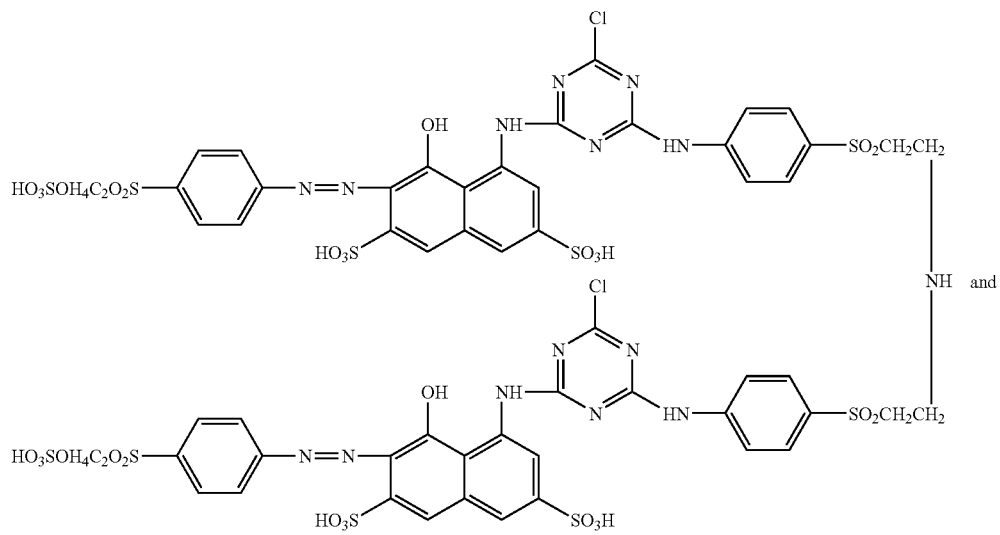

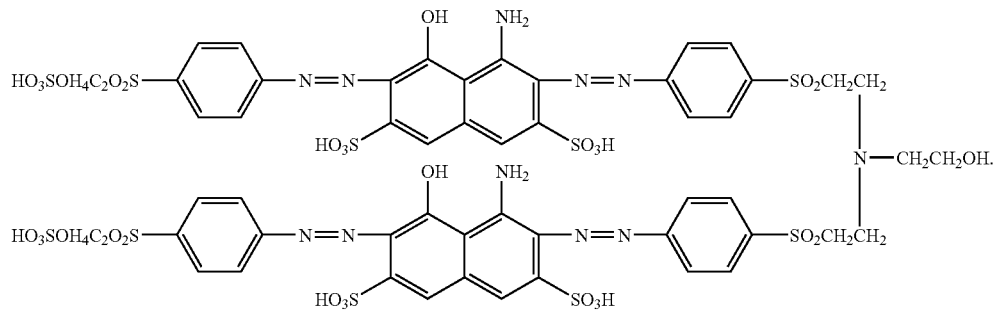

The dyestuff compounds of the present invention can be fixed on natural or regenerated cellulose fibers in various ways, such as cotton, hemp, linen, jute, ramie, mucilage rayon, as well as fibers blended fabrics containing hydroxyl groups. They can be applied to cellulose fibers by general dyeing methods, such as exhaustion dyeing, continuous dyeing, cold-pad-batch dyeing, printing or digital printing, and dyed products with high fixation, good build up and good wash-off can be obtained.

The dyeing or printing of the present invention can be proceeded by the conventional and usually known method. For example, exhaustion dyeing is applied by using separately or mixing the well-known inorganic salts (e.g. sodium sulfate and sodium chloride) and acid-binding agents (e.g. sodium carbonate, sodium hydroxide). The amount of inorganic salts and alkali does not matter. The inorganic salts and alkali can be added either once or several times into the dyeing bath through traditional methods. In addition, dyeing assistant agents (such as leveling agent, suspending agent and so on) can be added according to conventional method. The range of dyeing temperature is from 40° C. to 90° C. Preferably, the temperature for dyeing is from 40° C. to 70° C.

In the cold-pad-batch dyeing method, the material is padded by using the well-known inorganic salts (e.g. sodium sulfate and sodium chloride) and acid-binding agents (e.g. sodium carbonate, sodium hydroxide). The padded fabric is rolled and stored at room temperature to allow dye fixation to take place.

In the continuous dyeing method, two different methods exist. In the one-bath pad dyeing method, the material is padded according to the conventional method in the mixture of the well-known acid-binding agents (e.g. sodium carbonate or sodium bicarbonate) and the pad liquid. The resultant material is then dried and color fixed by baking or steaming.

In the two-bath pad dyeing method, the material is padded with a dye liquid and then dealt by a known inorganic neutral salt (e.g., sodium sulfate or sodium silicate). The dealt material is preferably dried and color fixed by baking or steaming as usual.

In the textile printing method, such as single printing method, the material is printed by printing slurry containing the known acid-binding agent (e.g., sodium bicarbonate) and is dried and color fixed by baking or steaming.

In the two-phase printing method, the material is dipped in a solution containing inorganic neutral salt (e.g., sodium chloride) and the known acid-binding agent (e.g., sodium hydroxide or sodium carbonate) in a high temperature of 90° C. or above to fix the color.

The dyeing or printing methods employed in the process of the present invention are not limited to the above methods.

Other objects, advantages, and novel features of the invention will become more apparent from the following detailed description when taken in conjunction with the accompanying drawings.

DETAILED DESCRIPTION OF THE PREFERRED EMBODIMENT

For convenience in the statement, the following examples are exemplified for a more concrete description. Many examples have been used to illustrate the present invention. The examples sited below should not be taken as a limit to the scope of the invention. For describing conveniently, the compound is expressed as free acid in the specification. When produced or used, the reactive dyestuffs of the present invention are often presented as water-soluble salts. The salts suitable for the present invention may be the alkaline metal salts, alkaline earth metal salts, ammonium salts or organic amine salts; preferably, the salts are sodium salts, potassium salts, lithium salts, ammonium salts or triethanolamine salts. Unless otherwise stated, the parts and percentage used in the following examples are based on weight, and the temperature is in Celsius degree (° C.).

EXAMPLE 1

2.66 parts of p-Aminophenyl-β-vinyl-sulphone are dissolved in 20 parts of acetonitrile, followed by the addition of 10 parts of 25% $NH_3$ (aq), and the reaction is performed for 24 hours at room temperature. The product of the formula (1) is obtained by crystallization, filtration and dryness.

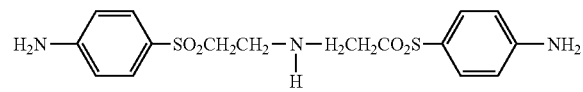

(1)

Micro analysis:
calculated for $C_{16}H_{21}N_3O_4S_2$C, 50.11; H, 5.52; N, 10.96. found: C, 50.07%; H, 5.39%, N, 10.32%. MS (m/z): calculated 383.5; found 384. $^1$H-NMR: 2.49 (2 H, d, 8-H), 2.63 (2 H, m, 9-H), 3.13 (2 H, t, J 6.78, 7-H), 3.37 (2 H, s, $NH_2$, 6.14 (2 H, s, $NH_2$), 6.63 (2 H, d, J 8.67, Ar—H), 7.44 (2 H, d, J 8.67, Ar—H). $^{13}$C-NMR: 38.5-40.2 (DMSO, o), 42.6 (1 C, $CH_2$), 55.4 (1 C, $CH_2$),112.6 (2 C, Ar), 123.6 (1 C, q-Ar), 129.4 (2 C, Ar), 153.5 (1 C, q-Ar).

EXAMPLE 2

2.66 parts of p-Aminophenyl-β-vinyl-sulphone are dissolved in 30 parts of acetonitrile, followed by the addition of 11.46 parts of 70% ethylamine, and the reaction is performed for 1 hour at 20° C. The product of the formula (65) is obtained by crystallization, filtration and dryness.

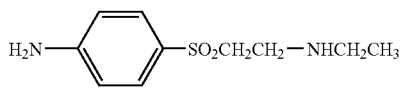

(65)

Micro analysis:
calculated for $C_{10}H_{16}N_2O_2S$: C, 52.36%; H, 7.03%; N, 12.21%. found: C, 51.68%; H, 7.26%; N, 12.04%. MS (m/z): calculated 229; found 229. $^1$H-NMR: 0.91 (3 H, m, 10-H), 2.38-2.45 (2 H, m, 9-H), 2.67 (2 H, t, J 7.16, 8-H), 3.19 (2 H, t, J 7.16, 7-H), 6.14 (2 H, s, $NH_2$), 6.64 (2 H, d, J 8.66, Ar—H), 7.45 (2 H, d, J 8.67, Ar—H). $^{13}$C-NMR: $^{13}$C: 15.3 (1 C, $CH_3$), 39.0-40.6 (DMSO, o), 43.3 (2 C, 2x $CH_2$), 55.9(1 C, $CH_2$), 113.1 (2C, Ar), 124.1 (1 C, q-Ar), 129.8(2C, Ar), 154.0(1 C, q-Ar).

Subsequently, 2.29 parts of the compound of the formula (65) react with 1.83 parts of p-Aminophenyl-β-vinyl-sulphone for 3 hours at 150° C. The product of the formula (2) is obtained by cooling, recrystallization in butanol, filtration and dryness.

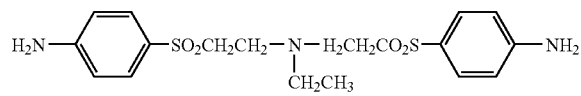

(2)

Micro analysis:
calculated for $C_{18}H_{25}N_3O_4S_2$: C, 52.53%; H, 6.12%; N, 10.21%. found: C, 53.22%; H, 6.45%; N, 9.36%. MS: (m/z): calculated 411.5; found 412.

EXAMPLE 3

1.83 parts of p-Aminophenyl-β-vinyl-sulphone are dissolved in 10 parts of acetonitrile, followed by the addition of 3.87 parts of 40% methylamine, and the reaction is performed for 4 hours at room temperature. The product of the formula (3) is obtained by recrystallization in butanol, filtration and dryness.

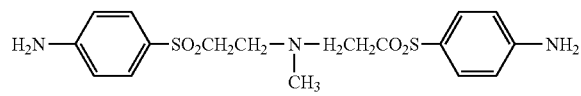

(3)

Micro analysis:
calculated for $C_{17}H_{23}N_3O_4S_2$: C, 51.37%; H, 5.83%; N, 10.57%. found: C, 51.37%; H, 5.79%; N, 10.37%. MS: (m/z): calculated 397.5; found 398.

EXAMPLE 4

1.83 parts of p-Aminophenyl-β-vinyl-sulphone and 0.45 part of aniline are added into a reaction tube, followed by the addition of 5 drops of acetic acid. The reaction is performed for 6 hours at 120° C. Finally, the product of the formula (4) is obtained by cooling, crystallization, filtration and dryness.

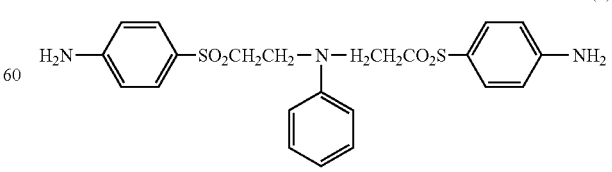

(4)

MS: (m/z): calculated for $C_{22}H_{25}N_3O_4S_2$ 459.6. found 460.

EXAMPLE 5

2.66 parts of m-Aminophenyl-β-vinyl-sulphone are added into 30 parts of ice water, followed by the addition of 10 parts of 25% $NH_3$ (aq). The reaction is performed for 24 hours at room temperature. Finally, the oily product of the formula (5) is obtained by thorough washing in utilization of 20%, pH 12 alkali solution.

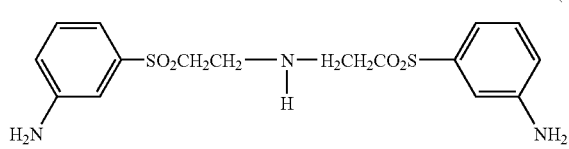

(5)

MS: (m/z): calculated for $C_{16}H_{21}N_3O_4S_2$ 383.5. found 384.

EXAMPLE 6

1.92 pats of the compound of the formula (5) prepared in Example 5 are added into 10 parts of acetic acid, followed by the addition of 0.42 part of sodium acetate and 9.0 parts of acetic anhydride. The reaction is performed for 2 hours at 40° C. Finally, the product of the formula (6) is obtained by column chromatography.

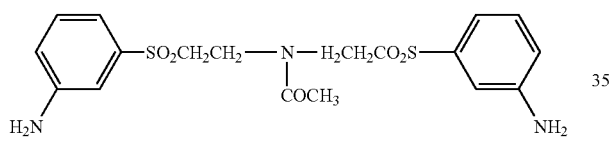

(6)

MS: (m/z): calculated for $C_{18}H_{23}N_3O_5S_2$ 425.5. found 425.

EXAMPLE 7

2.66 parts of p-Aminophenyl-β-vinyl-sulphone are dissolved in 20 parts of acetonitrile, followed by the addition of 20 parts of aqueous solution containing 3.25 parts of taurine. At room temperature, the pH value of reaction solution is adjusted to 9 by 20% $Na_2CO_3$ (aq) and the reaction is performed for 24 hours. The product of the formula (7) is obtained by crystallization, filtration and dryness.

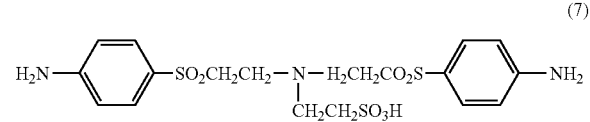

(7)

MS: (m/z): calculated for $C_{18}H_{25}N_3O_7S3$ 491.6. found 492.

EXAMPLES 8-51

According to the synthetic methods of Examples 1-7, the compounds of the following examples 8-51 are obtained.

TABLE 1

| Example | Structure |
|---|---|
| 8 | ![structure 8] (H₅C₂)HN–⟨benzene⟩–SO₂CH₂CH₂–NH–H₂CH₂CO₂S–⟨benzene⟩–NH(C₂H₅)  (8) |
| 9 | HO₃S, H₂N–⟨benzene⟩–SO₂CH₂CH₂–NH–H₂CH₂CO₂S–⟨benzene⟩–SO₃H, NH₂  (9) |
| 10 | H₃CO–⟨benzene⟩(H₂N)–SO₂CH₂CH₂–NH–H₂CH₂CO₂S–⟨benzene⟩(NH₂)–OCH₃  (10) |

TABLE 1-continued
| Example | Structure |
|---|---|
| 11 | 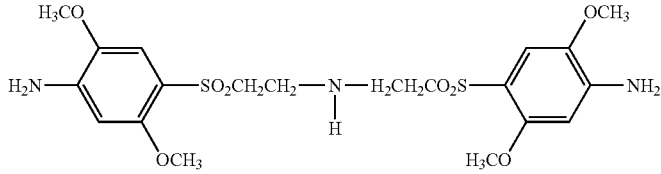 (11) |
| 12 | 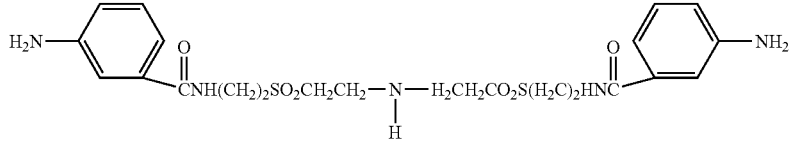 (12) |
| 13 | 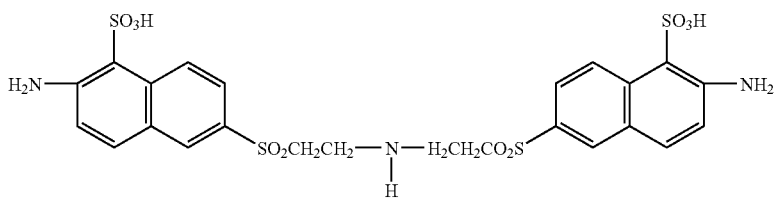 (13) |
| 14 | 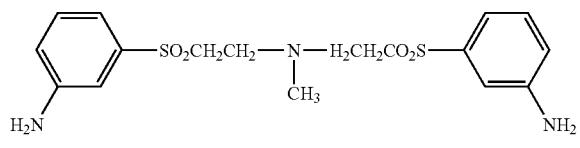 (14) |
| 15 | 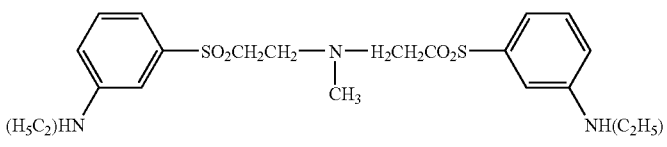 (15) |
| 16 | 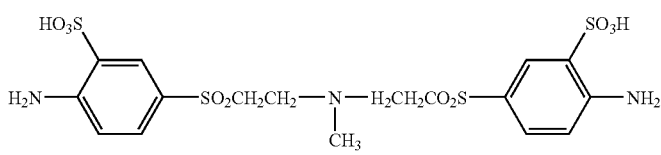 (16) |
| 17 | 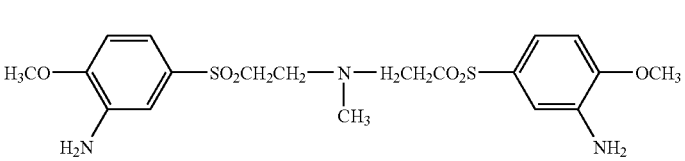 (17) |

TABLE 1-continued
| Example | Structure |
|---|---|
| 18 | 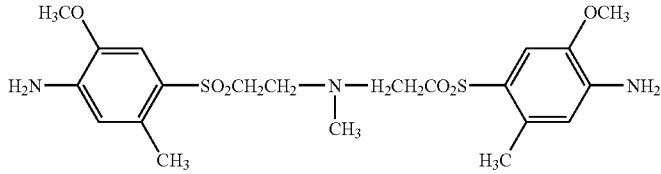 (18) |
| 19 | 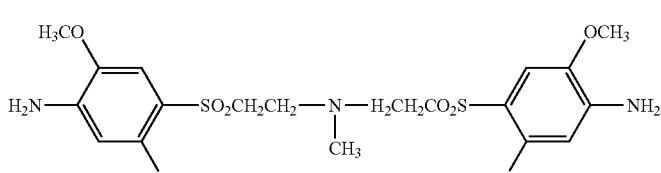 (19) |
| 20 | 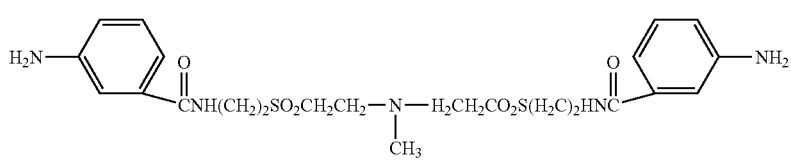 (20) |
| 21 | 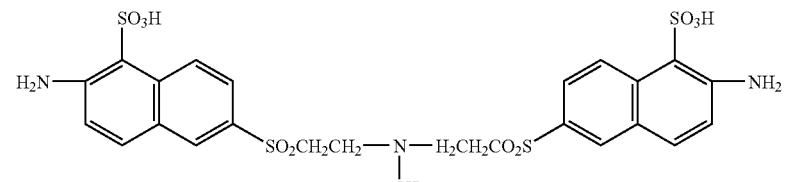 (21) |
| 22 | 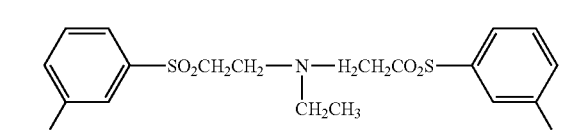 (22) |
| 23 | 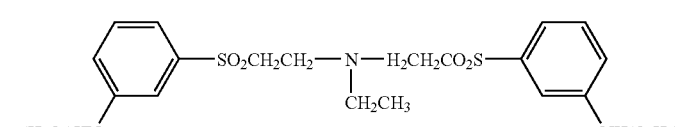 (23) |
| 24 | 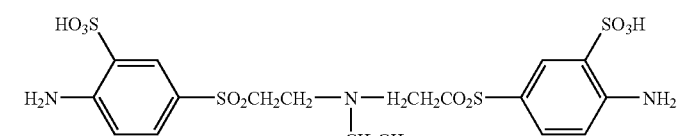 (24) |

TABLE 1-continued
| Example | Structure |
|---|---|
| 25 | 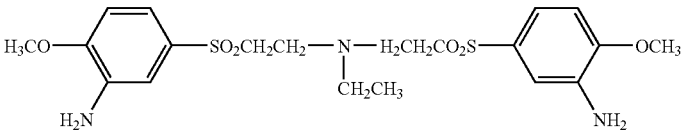<br>(25) |
| 26 | 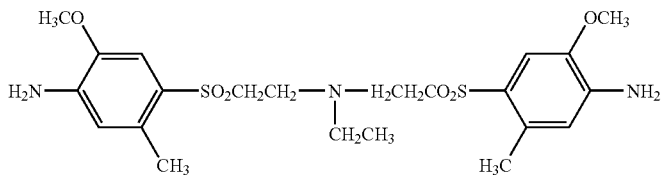<br>(26) |
| 27 | 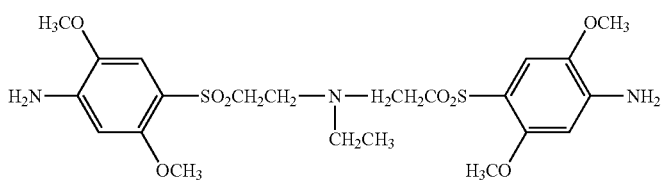<br>(27) |
| 28 | 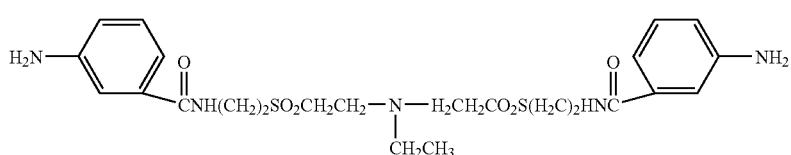<br>(28) |
| 29 | 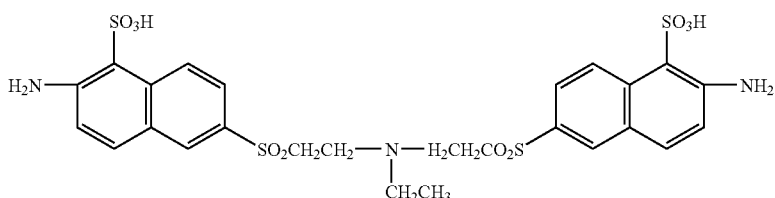<br>(29) |
| 30 | 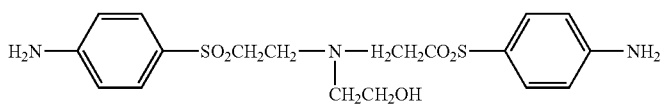<br>(30) |
| 31 | 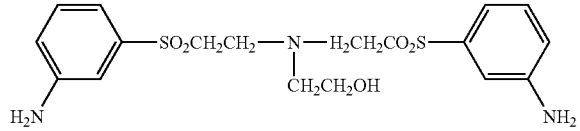<br>(31) |

TABLE 1-continued
| Example | Structure |
|---------|-----------|
| 32 | 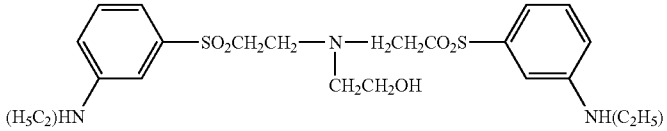 (32) |
| 33 | 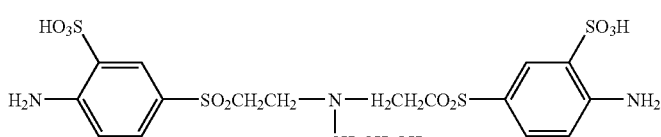 (33) |
| 34 | 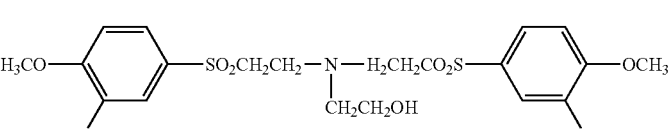 (34) |
| 35 | 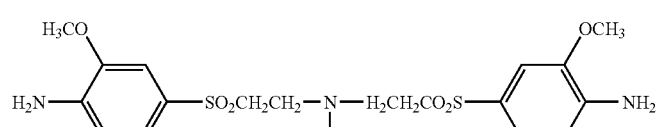 (35) |
| 36 | 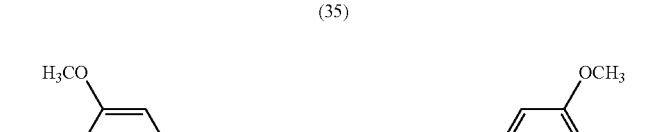 (36) |
| 37 | 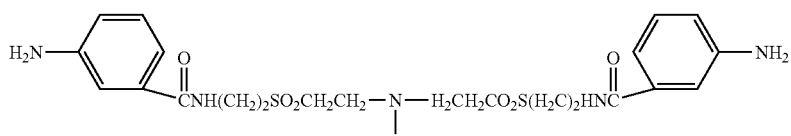 (37) |
| 38 |  (38) |

TABLE 1-continued
| Example | Structure |
|---|---|
| 39 | 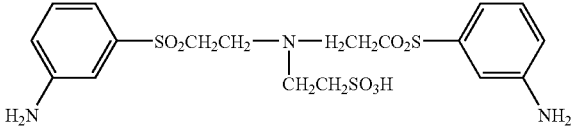 (39) |
| 40 | 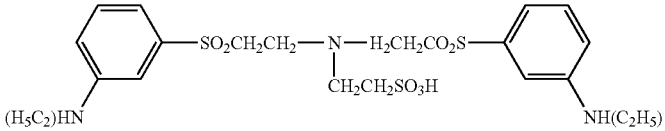 (40) |
| 41 | 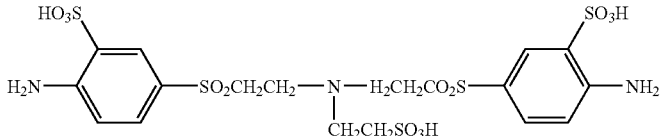 (41) |
| 42 | 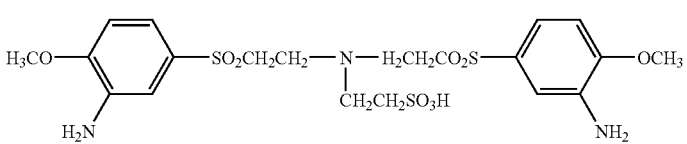 (42) |
| 43 | 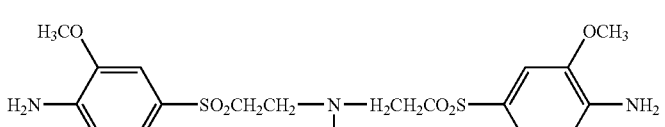 (43) |
| 44 |  (44) |
| 45 | 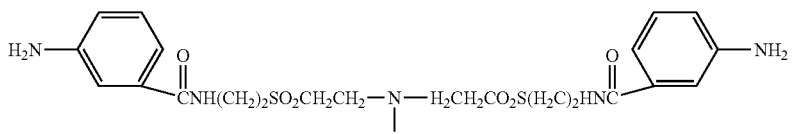 (45) |

TABLE 1-continued
| Example | Structure |
|---|---|
| 46 | 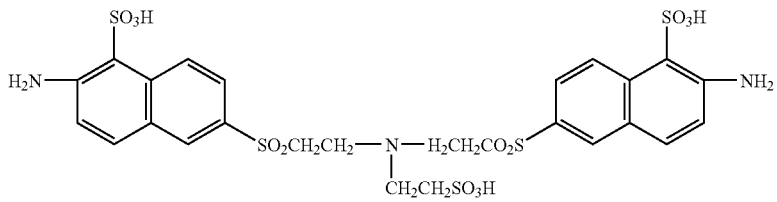<br>(46) |
| 47 | 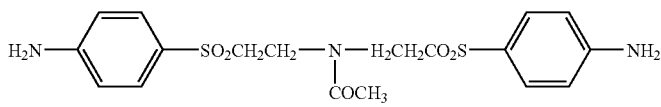<br>(47) |
| 48 | 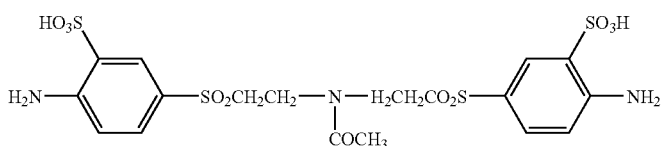<br>(48) |
| 49 | 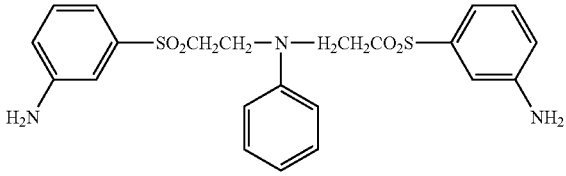<br>(49) |
| 50 | 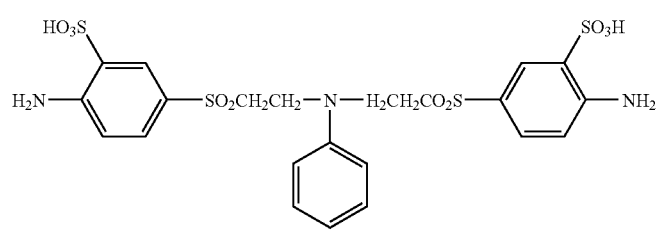<br>(50) |
| 51 | 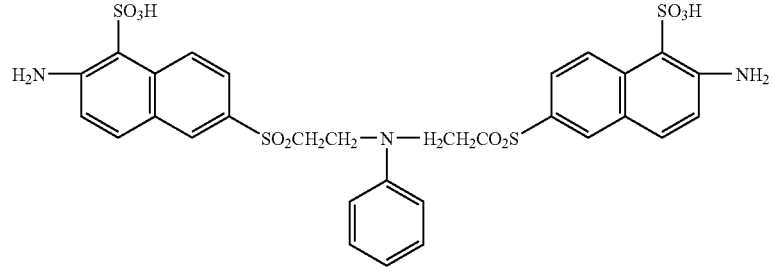<br>(51) |

EXAMPLE 52

3.66 parts of p-Aminophenyl-β-vinyl-sulphone are dissolved in 40 parts of acetonitrile, followed by the addition of 1.22 parts of ethanolamine, and the reaction is performed for 12 hours at room temperature. The product of the formula (66) is obtained by crystallization, filtration and dryness.

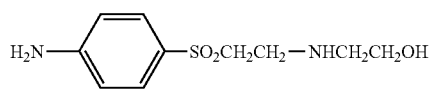
(66)

Micro analysis:
calculated for $C_{10}H_{16}N_2O_3S$: C, 49.17%; H, 6.60%; N, 11.46%. found: C, 48.92%; H, 6.63%; N 11.40%. MS (m/z): calculated 244.3; found 245. $^1$H-NMR: 1.81 (1 H, s, NH), 2.45-2.49 (m, DMSO), 2.67-2.72(2 H, m, 8-H), 3.18-3.23 (2 H, m, 7-H), 4.44-4.48 (1 H, t, J 4.90, OH), 6.14 (2 H, s, NH$_2$), 6.63 (2 H, d, J 8.29, Ar—H), 7.45 (2 H, d, J 8.67, Ar—H). $^{13}$C-NMR: 38.5-40.2 (m, DMSO), 43.0 (1 C, CH$_2$), 51.1 (1 C, CH$_2$), 55.6 (1 C, CH$_2$), 60.1 (1 C, CH$_2$), 112.6 (2 C, Ar), 123.7 (1 C, q-Ar), 129.4 (2 C, Ar), 153.5 (1 C, q-Ar).

Subsequently, 5 parts of m-Aminophenyl-β-vinyl-sulphone are dissolved in 50 parts of acetonitrile, followed by the addition of 5 parts of the compound of the formula (66), and the reaction is performed for 12 hours at room temperature. The product of the formula (52) is obtained by crystallization, filtration and dryness.

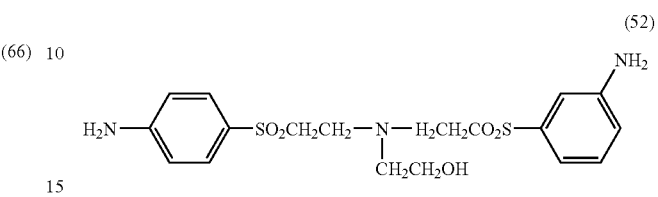
(52)

Micro analysis:
calculated for $C_{18}H_{25}N_3O_5S_2$: C, 50.57%; H, 5.90%; N, 9.83%. found: C, 50.31%; H, 5.85%; N, 9.71%. MS: (m/z): calculated 427.6; found 428.

EXAMPLES 53-64

According to the synthetic method of Example 52, the compounds of the following examples 53-64 are obtained.

TABLE 2

| Example | Structure |
|---|---|
| 53 | ![](structure 53) H$_2$N—C$_6$H$_4$—SO$_2$CH$_2$CH$_2$—N(CH$_2$CH$_2$OH)—H$_2$CH$_2$CO$_2$S—C$_6$H$_3$(SO$_3$H)—NH$_2$ (53) |
| 54 | ![](structure 54) HO$_3$S, H$_2$N—C$_6$H$_3$—SO$_2$CH$_2$CH$_2$—N(CH$_2$CH$_2$OH)—H$_2$CH$_2$CO$_2$S—C$_6$H$_2$(OCH$_3$)(CH$_3$)—NH$_2$ (54) |
| 55 | H$_2$N—C$_6$H$_4$—SO$_2$CH$_2$CH$_2$—N(CH$_2$CH$_3$)—H$_2$CH$_2$CO$_2$S—C$_6$H$_4$—NH$_2$ (55) |
| 56 | H$_2$N—C$_6$H$_4$—SO$_2$CH$_2$CH$_2$—N(CH$_2$CH$_3$)—H$_2$CH$_2$CO$_2$S—C$_6$H$_3$(SO$_3$H)—NH$_2$ (56) |

TABLE 2-continued

| Example | Structure |
|---|---|
| 57 | Structure (57): 4-amino-3-methoxyphenyl-SO₂CH₂CH₂-N(CH₂CH₃)-H₂CH₂CO₂S-(4-amino-3-sulfophenyl) |
| 58 | Structure (58): 4-aminophenyl-SO₂CH₂CH₂-N(CH₂CH₃)-H₂CH₂CO₂S-(2-amino-1-sulfonaphthalen-6-yl) |
| 59 | Structure (59): 4-aminophenyl-SO₂CH₂CH₂-N(CH₂CH₂SO₃H)-H₂CH₂CO₂S-(3-aminophenyl) |
| 60 | Structure (60): 4-aminophenyl-SO₂CH₂CH₂-N(CH₂CH₂SO₃H)-H₂CH₂CO₂S-(4-amino-3-sulfophenyl) |
| 61 | Structure (61): 4-amino-2-methoxy-5-methylphenyl-SO₂CH₂CH₂-N(CH₂CH₂SO₃H)-H₂CH₂CO₂S-(4-amino-3-sulfophenyl) |
| 62 | Structure (62): 4-aminophenyl-SO₂CH₂CH₂-N(phenyl)-H₂CH₂CO₂S-(4-amino-3-sulfophenyl) |

TABLE 2-continued

| Example | Structure |
|---|---|
| 63 | 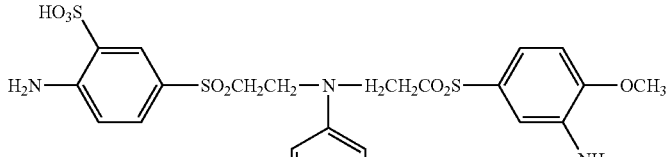 (63) |
| 64 | 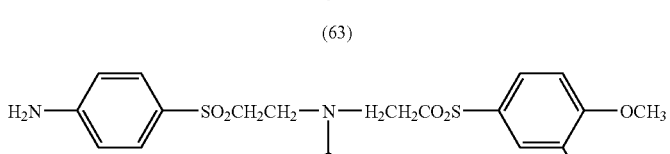 (64) |

APPLICATION EXAMPLE 1

1.92 parts of N,N-di-[2-(4'-aminophenyl)-sulphonyl-ethyl]-amine, the compound of the formula (1), are dispersed in 100 parts of ice water, and then the powders of the red compound of the formula (67) are added therein.

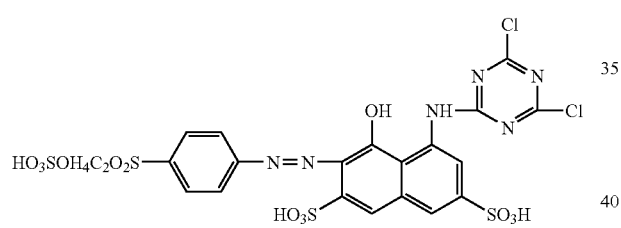

(67)

Subsequently, the pH value of the reaction solution is adjusted to 5.5 by NaHCO$_3$ with continuous stirring at a temperature in the range of 15° C. to 25° C. until the condensation reaction is accomplished. The red dyestuff of the formula (68) is obtained by salting-out, filtration and wash with brine water. The dyestuff exhibits excellent build up for exhaustion dyeing cellulose fibers.

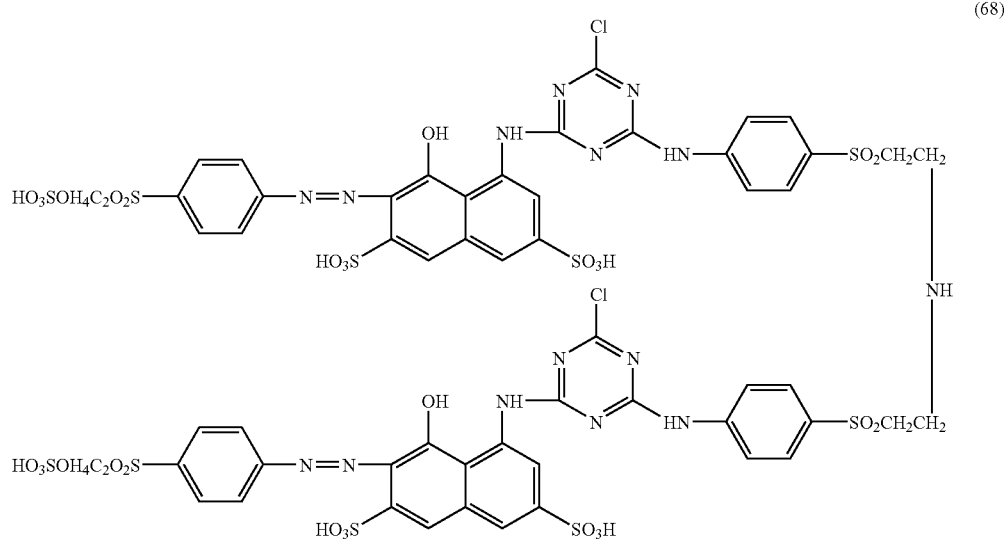

(68)

APPLICATION EXAMPLE 2

2.13 parts of N,N-bis-[2-(4'-Aminophenyl)sulphonyl-ethyl]-hydroxyethylamine, the compound of the formula (30), are dispersed in 100 parts of ice water, and then 3.0 parts of 32% HCl are added therein with thorough stirring, followed by the addition of 0.69 part of sodium nitrite with continuous stirring at a temperature in the range of 0° C. to 5° C. until the diazotization is accomplished. 3.19 parts of 1-hydroxy-8-amino-naphthalene-3,6-disulfonic acid powder are added into the above solution with continuous stirring until the coupling reaction is accomplished. The product of the formula (69) is obtained.

the dyeing vessel to be 75 parts in total. After that, 5 parts of 320 g/l soda ash are added to the dyeing vessel. 4 parts of pre-wet woven cotton fabric are put into the dyeing solution, followed by covering and locking the dyeing vessel, and shaking the dyeing vessel to survey the dye. Then, the dyeing vessel is put into a thermostatic bath, followed by switching on the rotating knob. The temperature is raised to 60° C. in 30 minutes and then the temperature is kept for 60 minutes for fixation. After dyeing, the dyed fabric is washed with cold water, followed by washing, dehydrating them and drying. Finally, a navy blue fabric with good build up and good tinctorial yield is obtained.

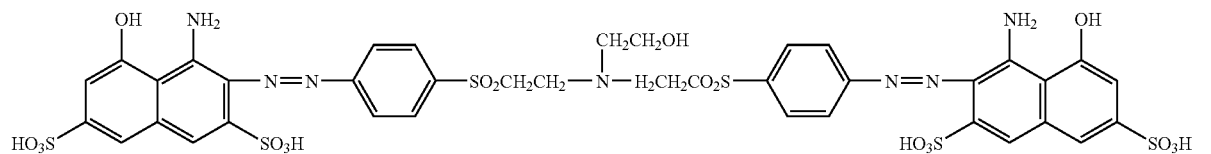

(69)

Subsequently, 2.81 parts of 4-β-sulfatoethylsulfone-aniline are dispersed in 30 parts of ice water, and then 3.0 parts of 32% HCl aqueous solution are added therein with thorough stirring, followed by the addition of 0.69 part of sodium nitrite aqueous solution with continuous stirring at a temperature in the range of 0° C. to 5° C. until the diazotization is accomplished. The coupling compound afforded by the aforementioned process is added therein, and the pH value of the reaction solution is adjusted to 5 by $NaHCO_3$ with continuous stirring at a temperature in the range of 15° C. to 25° C. until the coupling reaction is accomplished. The navy blue product of the following formula (70) is obtained by salting-out, filtration and wash with brine water. The dyestuff exhibits excellent build up for exhaustion dyeing cellulose fibers.

From the foregoing description, the technology according to the present invention achieves the objects of the invention and conforms to the patent requirements of novelty, inventive step and industrial applicability. Although the present invention has been explained in relation to its preferred examples, it is to be understood that many other possible modifications and variations can be made without departing from the scope of the invention as hereinafter claimed.

What is claimed is:

1. A bridge compound with an N,N-dialkylamino group of the following formula (I),

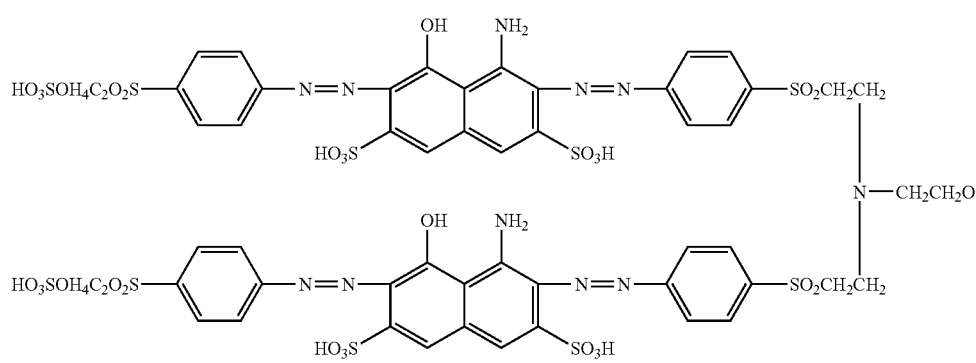

(70)

TESTING EXAMPLE 1

1 part of the dyestuff of formula (70) prepared in Application Example 2 is dissolved in 100 parts of distilled water to prepare a stock solution. 20 parts of the dye solution are poured into a dyeing vessel. 4.8 parts of Glauber's Salt are added to the dyeing vessel and then distilled water is poured therein to make up the total amount of the dyeing solution in

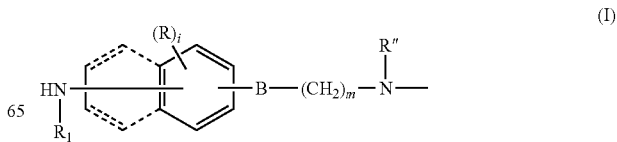

(I)

-continued

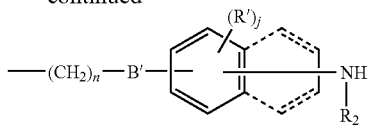

wherein,
R and R' each independently are selected from the group consisting of hydrogen, halogen, hydroxyl, carboxyl, sulfo, nitro, cyano, $C_{1-4}$ alkyl, $C_{1-4}$ alkoxy, ureido and amido;
$R_1$ and $R_2$ each independently are hydrogen, or $C_{1-4}$ alkyl;
R" is hydrogen, $C_{1-4}$ alkylcarbonyl, phenyl, $C_{1-4}$ alkyl, or $C_{1-4}$ alkyl substituted by halogen, hydroxyl, carboxyl or sulfo;
B and B' each independently are selected from the group consisting of —$SO_2$— and —CONH—$(CH_2)_n$—$SO_2$—;
i and j are integers independent of one another between 0 to 3; and
m and n are integers independent of one another between 2 to 4.

2. The bridge compound as claimed in claim 1, wherein the compound of the formula (I) is the compound of the following formula (Ia),

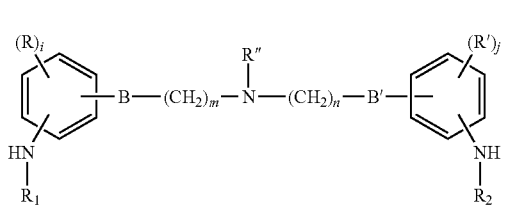

and R, R', R", $R_1$, $R_2$, B, B', i, j, m and n are defined the same as claim 1.

3. The bridge compound as claimed in claim 1, wherein R and R' each independently are selected from the group consisting of hydrogen, sulfo, methyl and methoxy.

4. The bridge compound as claimed in claim 1, wherein R" is selected from the group consisting of hydrogen, methyl, ethyl, —$C_2H_4OH$, —$C_2H_4SO_3H$, —$COCH_3$ and phenyl.

5. The bridge compound as claimed in claim 1, wherein R and R' are the same and are selected from the group consisting of hydrogen, halogen, hydroxyl, carboxyl, sulfo, nitro, cyano, $C_{1-4}$ alkyl, $C_{1-4}$ alkoxy, ureido and amido; $R_1$ and $R_2$ are the same and are hydrogen, or $C_{1-4}$ alkyl; B and B' are the same and are selected from the group consisting of —$SO_2$— and —CONH—$(CH_2)_n$—$SO_2$—; i and j are the same and are integers between 0 to 3; and m and n are the same and are integers between 2 to 4.

6. The bridge compound as claimed in claim 1, wherein the compound of the formula (I) is the compound of the following formula (1),

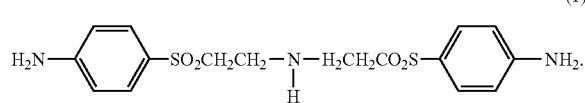

7. The bridge compound as claimed in claim 1, wherein the compound of the formula (I) is the compound of the following formula (2),

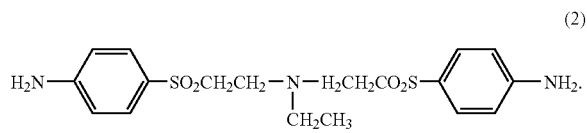

8. The bridge compound as claimed in claim 1, wherein the compound of the formula (I) is the compound of the following formula (3),

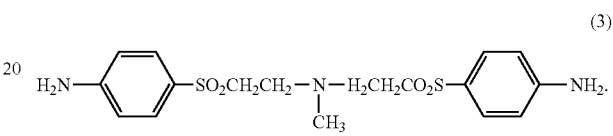

9. The bridge compound as claimed in claim 1, wherein the compound of the formula (I) is the compound of the following formula (4),

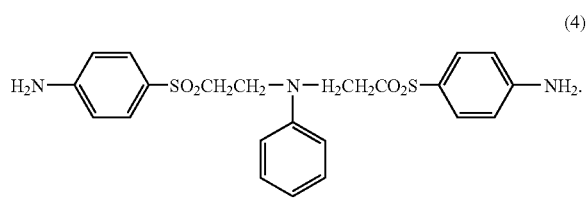

10. The bridge compound as claimed in claim 1, wherein the compound of the formula (I) is the compound of the following formula (5),

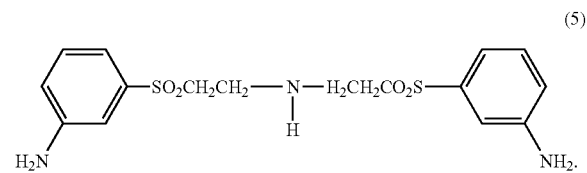

11. The bridge compound as claimed in claim 1, wherein the compound of the formula (I) is the compound of the following formula (6),

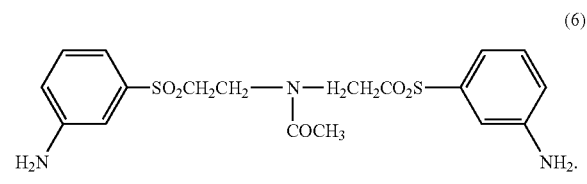

12. The bridge compound as claimed in claim 1, wherein the compound of the formula (I) is the compound of the following formula (7),
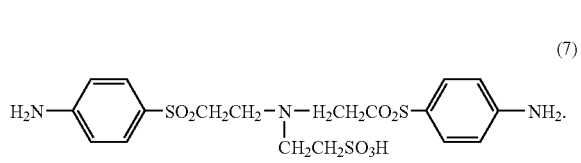
13. The bridge compound as claimed in claim 1, wherein the compound of the formula (I) is the compound of the following formula (52),
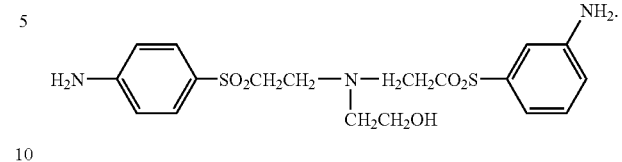
14. A dyestuff compound with an N,N-dialkylamino group of the following formula (68),
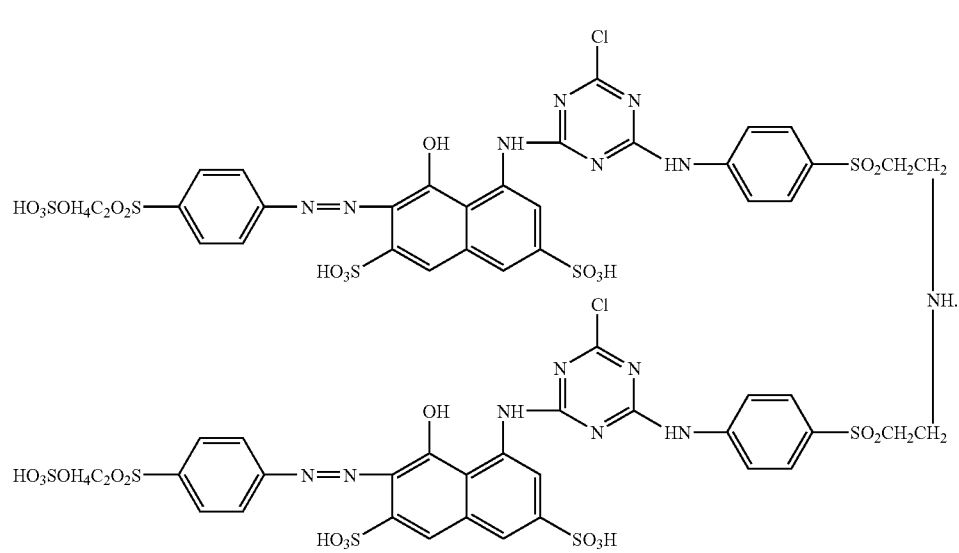
* * * * *